United States Patent [19]

Nawata et al.

[11] Patent Number: 5,531,225
[45] Date of Patent: Jul. 2, 1996

[54] MEASURING APPARATUS FOR A COMPONENT CONTAINED IN EXHALATION

[75] Inventors: Katsumi Nawata, Susono; Fumihiro Ushijima, Gotenba; Toshiyuki Taguchi, Okazaki; Hazime Inagaki, Nagoya, all of Japan

[73] Assignees: Toyota Jidosha Kabushiki Kaisha, Toyota; Kabushiki Kaisha Toyota Chuo Kenkyusho, Aichi-gun, both of Japan

[21] Appl. No.: 322,426

[22] Filed: Oct. 13, 1994

[30] Foreign Application Priority Data

Oct. 15, 1993 [JP] Japan .................................. 5-258712
Oct. 18, 1993 [JP] Japan .................................. 5-260048

[51] Int. Cl.⁶ ...................................................... A61B 5/08
[52] U.S. Cl. .......................... 128/719; 73/23.3; 180/272; 340/576; 422/84
[58] Field of Search ..................... 128/716, 719; 422/84; 180/272; 340/576; 73/23.3

[56] References Cited

U.S. PATENT DOCUMENTS

| | | | |
|---|---|---|---|
| 3,815,087 | 6/1974 | Hirano et al. | 180/272 |
| 3,831,707 | 8/1974 | Takeuchi | 180/272 |
| 3,855,573 | 12/1974 | Honda et al. | 180/272 |
| 4,809,810 | 3/1989 | Elfman et al. | 180/272 |
| 5,425,374 | 6/1995 | Ueda et al. | 128/719 |

FOREIGN PATENT DOCUMENTS

| | | |
|---|---|---|
| 51-21698 | 7/1976 | Japan . |
| 56-18898 | 5/1981 | Japan . |
| 63-172953 | 7/1988 | Japan . |
| 6-197897 | 7/1994 | Japan . |

*Primary Examiner*—Lee S. Cohen
*Attorney, Agent, or Firm*—Cushman Darby & Cushman

[57] ABSTRACT

There is provided a measuring apparatus for alcohol contained in an exhalation, the measuring apparatus measuring concentration of alcohol with a high accuracy in a short time. An alcohol sensor is provided inside an air passage to measure concentration of alcohol contained in air passing through the air passage. The alcohol sensor has a sensing element for sensing alcohol and a heating element for heating the sensing element. A suction pump is provided to the air passage so as to suction air from an inlet of the air passage. The sensing element is situated inside an air trapping chamber so that the air flowing through the air passage does not directly hit the sensing element.

5 Claims, 19 Drawing Sheets

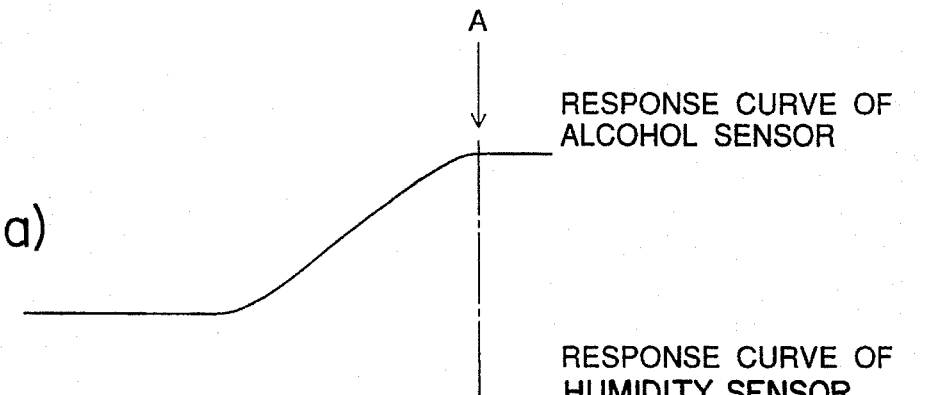
FIG. 19(a) RESPONSE CURVE OF ALCOHOL SENSOR
FIG. 19(b) RESPONSE CURVE OF HUMIDITY SENSOR
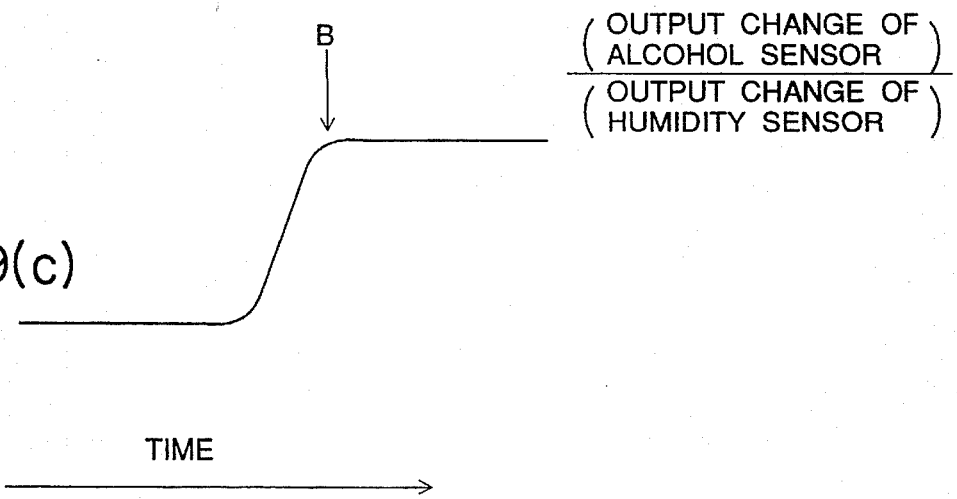
FIG. 19(c) (OUTPUT CHANGE OF ALCOHOL SENSOR) / (OUTPUT CHANGE OF HUMIDITY SENSOR)
TIME

MEASURING APPARATUS FOR A COMPONENT CONTAINED IN EXHALATION

BACKGROUND OF THE INVENTION

1. Field of the Invention

The present invention generally relates to a measuring apparatus for a component contained in an exhalation, and more particularly to a measuring apparatus which measures concentration of alcohol contained in an exhalation of a driver of a vehicle.

2. Description of the Related Art

Japanese Patent Publication No. 51-21698 and U.S. Patent Ser. No. 3,855,573 disclose an apparatus which measures concentration of alcohol contained in an exhalation of a driver of a vehicle so as to enable an operation of the vehicle in accordance with a result of the measurement.

This apparatus comprises a tubular member, a suction pump and an alcohol sensor. The suction pump connected to one end of the tubular member, and the other hand of the tubular member is located near a driver's seat of a vehicle. The alcohol sensor is positioned in the tubular member. A portion of an exhalation of the driver is suctioned into the tubular member by the suction pump so that concentration of alcohol contained in the exhalation of the driver is measured by the alcohol sensor. When the concentration of the alcohol measured by the alcohol sensor reaches a predetermined level, the vehicle is rendered not to be operative.

As for the alcohol sensor provided in the tubular member, a heating type alcohol sensor such as described in Japanese Laid-Open Patent Application No. 63-172953 is used. This alcohol sensor comprises a sensing element made of a metal oxide semiconductor such as $SnO_2$. The sensing element is usually heated at 350° to 400° C. in use.

The above-mentioned conventional technique has some problems described below

A first problem is related to inaccuracy due to air movement of around the alcohol sensor. As mentioned above, the alcohol sensor is used at a high temperature such as 350° to 400° C. If a fluctuation of an air flow is generated around the alcohol sensor, heat is irregularly released from the alcohol sensor, and thus the alcohol sensor cannot be maintained at a constant temperature.

This is also a problem when other sensors are provided near the alcohol sensor so as to obtain more accurate measurement because provision of other sensors may cause a turbulent flow of air passing through the alcohol sensor. Adversely, other sensors may be affected by heat released from the alcohol sensor, and thus an accuracy of measurement may be decreased.

A second problem is related to a condition of exhalation such as a direction and an amount of exhalation. Such condition is dependent on a seating position and a physique of each driver, and thus a variation in results of measurement may occur. It is difficult for the driver to exhale a predetermined amount of air in a predetermined direction every time.

If a suction capacity of the suction pump is set for a condition in which the driver sits at a maximum distance from the inlet port of the measuring apparatus, a sufficient exhalation may be suctioned. However in such a case, accuracy of the alcohol sensor may be deteriorated because large amount of air passes around the alcohol sensor which condition results in undesired cooling of the alcohol sensor to be used at a high temperature as mentioned above.

Additionally, waiting time for the alcohol sensor reaching a predetermined temperature may increase due to the cooling effect of the suctioned air. This causes the driver to wait for a long time.

A third problem is related to a possible measuring error due to a mixture ratio of an exhalation of a driver and air in the vehicle. If much air relative to the exhalation is suctioned into the measuring apparatus, concentration of the alcohol to be measured becomes less than a correct concentration of alcohol.

In order to eliminate the above problem, Japanese Patent Publication No. 56-18898 suggested use of a pressure sensor so as to measure a pressure change in the tubular member. This method is effective for preventing a deceiving action such as closing of the tubular member. However, this method is not accurate sufficient for determining whether the exhalation is actually introduced into the tubular member or only surrounding air is introduced by other means.

Japanese Patent Publication No. 56-18898 teaches determining means for determining whether an exhalation is actually introduced in accordance with changes in humidity and temperature of the air to be measured. This method still has a problem in that the result of measurement may be fabricated by putting wet hand over an inlet port for the air to be measured. Additionally, providing sensors other than alcohol sensor in the tubular member may generate a turbulence in the suctioned air which condition affects the accuracy of the alcohol sensor. Further, heating of the alcohol sensor may affect other sensors which may sensitive to a temperature change.

A fourth problem is related to a time spent on a measurement performed by the alcohol sensor. The conventional alcohol sensor takes a relatively long response time (from a time when alcohol makes contact with the alcohol sensor to a time when an output of the alcohol sensor becomes stable at a value corresponding to the concentration of the alcohol). The driver may feel uncomfortable for waiting for such a long response time.

SUMMARY OF THE INVENTION

It is a general object of the present invention to provide an improved and useful measuring apparatus for a component contained in an exhalation in which measuring apparatus the above-mentioned disadvantages are eliminated.

A more specific object of the present invention is to provide a measuring apparatus for alcohol contained in an exhalation which measuring apparatus performs a measuring operation with a high accuracy in a short time.

Another object of the present invention is to provide a measuring apparatus for a component contained in an exhalation which measuring apparatus performs a correction for a variation in suctioned amount of the exhalation.

Another object of the present invention is to provide a measuring apparatus for alcohol contained in an exhalation which measuring apparatus can discriminate actual alcohol contained in the exhalation from alcohol generated from other sources so as to increase an accuracy of measurement of alcohol contained in the exhalation.

Another object of the present invention is to provide a measuring apparatus for alcohol contained in an exhalation which measuring apparatus can determine whether an air being measured actually contains an exhalation so as to prevent an erroneous determination of non-presence of alcohol.

In order to achieve the above-mentioned objects, there is provided according to one aspect of the present invention, an alcohol measuring apparatus for measuring a concentration of alcohol contained in an exhalation, the alcohol measuring apparatus comprising:

an air passage having an inlet being positioned in a range where the exhalation to be measured reaches;

an alcohol sensor being provided inside the air passage downstream of the inlet for measuring a concentration of alcohol contained in air passing through the inlet, the alcohol sensor having an air trapping chamber, a sensing element in the air trapping chamber for sensing alcohol and a heating element for heating the sensing element; and suction means connected to the air passage so as to suction an air from the inlet of said air passage.

There is provided according to another aspect of the present invention an alcohol measuring apparatus for measuring a concentration of alcohol contained in an exhalation, the alcohol measuring apparatus comprising:

an air passage having an inlet being positioned in a range where the exhalation to be measured reaches;

a humidity sensor being provided downstream of the inlet in the passage;

an alcohol sensor being provided downstream of the humidity sensor near the humidity sensor inside the air passage for measuring a concentration of alcohol contained in air passing through the air passage, the alcohol sensor having a sensing element for sensing alcohol and a heating element for heating the sensing element; and suction means provided to the air passage so as to suction an air from the inlet of said air passage, There is provided according to another aspect of the present invention a measuring apparatus for measuring a component contained in an exhalation exhaled from a person, the measuring apparatus comprising:

an air passage having an inlet being positioned in a range where the exhalation to be measured reaches; a sensor being provided downstream of the inlet inside said air passage for measuring a concentration of a component of the exhalation contained in air passing through the inlet;

suction means provided to the air passage so as to suction an air from the inlet of the air passage;

seat position detecting means for detecting a position of seat on which the person is sitting, and outputting a signal representing a distance between the inlet of the air passage and the person; and regulating means for regulating an amount of the air being suctioned from the inlet of said air passage by controlling the suction means in accordance with the signal supplied by the seat position detecting means.

There is provided according to another aspect of the present invention an alcohol measuring apparatus for measuring a concentration of alcohol contained in an exhalation, the alcohol measuring apparatus comprising:

a suction unit having an air passage for introducing a mixture of air and exhalation, and suction means connected to the air passage for suctioning the mixture;

a sulfide sensor, provided in the air passage upstream of the suction means, for sensing a sulfide contained in the mixture;

a humidity sensor, provided in the air passage upstream of the suction means, for sensing water vapor contained in the mixture;

an alcohol sensor, provided in the air passage upstream of the suction means, for sensing alcohol contained in the mixture;

an exhalation identification unit for determining a presence of the exhalation in the mixture in accordance with a ratio of an output from the sulfide sensor to an output from the humidity sensor; and an alcohol concentration determining unit for determining the concentration of alcohol contained in the exhalation in accordance with a ratio of an output from the alcohol sensor to the output from the humidity sensor.

Other objects, features and advantages of the present invention will become more apparent from the following detailed description when read in conjunction with the accompanying drawings.

BRIEF DESCRIPTION OF THE DRAWINGS

FIG. 19 is an illustration showing response curves of an alcohol sensor and a humidity sensor and a curve of a ratio of an output change of the alcohol sensor to an output change of the humidity sensor;

DETAILED DESCRIPTION OF THE PREFERRED EMBODIMENTS

Figure 1:
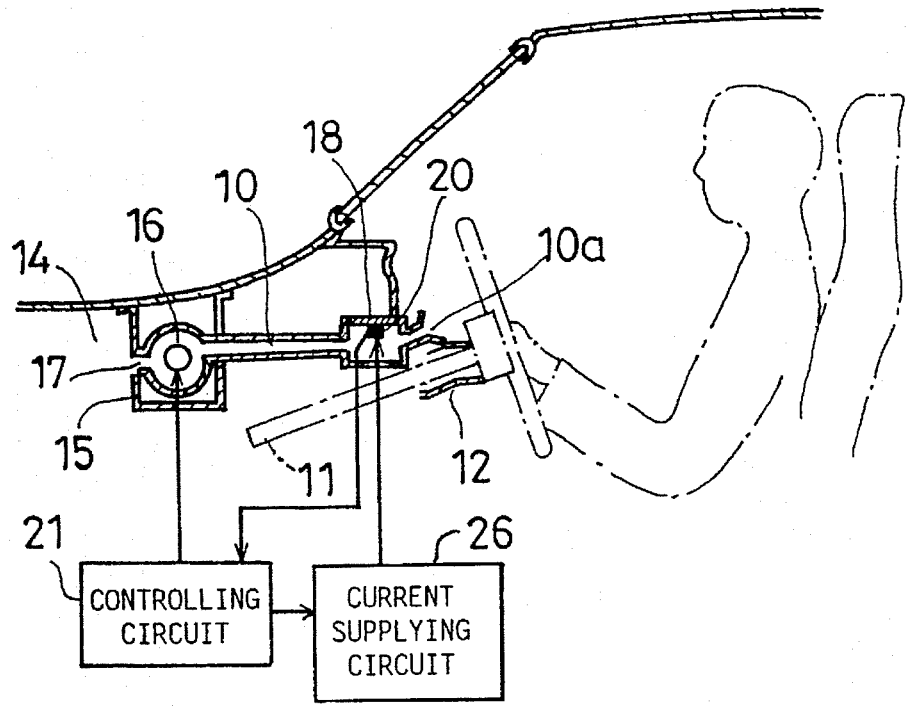
FIG. 1 is an illustration of a first embodiment of an alcohol measuring apparatus according to the present invention.

A description will now be given of a first embodiment of an alcohol measuring apparatus according to the present invention. FIG. 1 is an illustration of the first embodiment according to the present invention. The first embodiment according to the present invention is a measuring apparatus for measuring concentration of alcohol contained in an exhalation of a driver of a vehicle. The measuring apparatus is provided in the vehicle near the driver.

The measuring apparatus comprises an air passage 10 and an attaching unit 15. An inlet 10a at the end of the of the air passage 10 is fixed on a cover 12 of a steering column 11, and formed as a horn-like shape so as to effectively collect an exhalation of the driver. The other end of the air passage 10 is inserted into the attaching unit 15 attached in an engine compartment 14, and connected to a suction pump 16 located in the attaching unit 15. A mixture gas of exhalation and air suctioned into the air passage 10 is exhausted from an exhaust port 17 formed on a wall of the attaching unit 15 via the suction pump 16.

A sensor casing 18 is provided downstream near the inlet 10a. An alcohol sensor 20 is provided in the sensor casing 18. The alcohol sensor 20 is provided for measuring alcohol component contained in a mixture of exhalation and surrounding air suctioned into the sensor casing 18.

Figure 2:
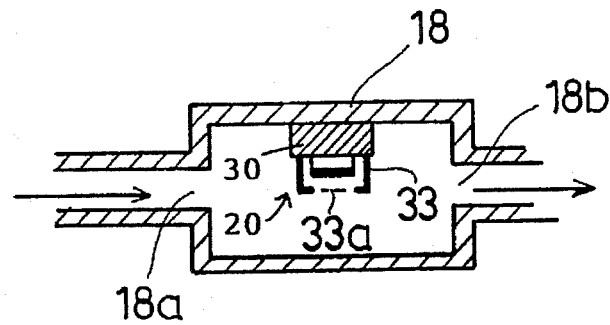
FIG. 2 is an enlarged cross sectional view of a sensor casing shown in FIG. 1.

FIG. 2 is an enlarged cross sectional view of the sensor casing 18. A base 30 of the alcohol sensor 20 is attached on a top wall of the sensor near the center thereof. An air flows through the sensor casing 18 from an upstream opening 18a to a downstream opening 18b as shown by arrows in the figure.

Figure 3A:
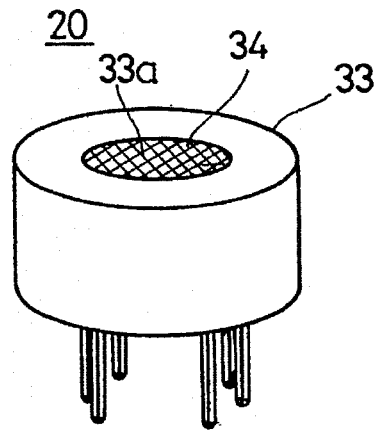
FIG. 3A is a perspective view of an alcohol sensor shown in FIG. 1.
Figure 3B:
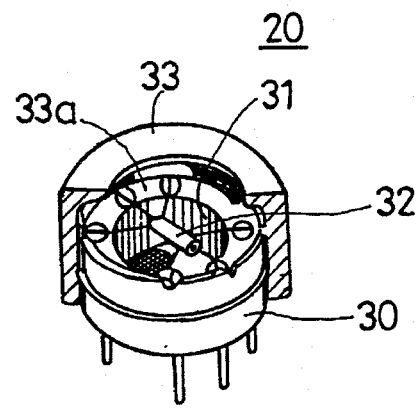
FIG. 3B is a partially cut away perspective view of the alcohol sensor shown in FIG. 1.

FIG. 3A is a perspective view of the alcohol sensor 18, and FIG. 3B is a partially cut away perspective view of the alcohol sensor 18. The alcohol sensor 20 comprises the base 30, a heater coil 31 and a sensing element 32. The heater coil 31 and the sensing element 32 are attached on the base 30 so that the heater coil 31 surrounds the sensing element 32. As for the sensing element 32, for example, a semiconductor made from a sintered tin oxide ($SnO_2$) is used. The heater coil 31 is heated by supplying electric power so that the sensing element 32 is heated at 350° to 400° C. In this heated condition, the sensing element 32 outputs a voltage signal corresponding to concentration of alcohol contained in an air surrounding the sensing element 32. The heater coil 31 and the sensing element 32 are covered with a cup-shaped cover 33 having an opening 33a from which an air flows into inside the cover 33. The opening 33a is provided with a mesh 34 to prevent foreign matter from entering into the cover 33. The cover 33 together with the base 30 forms an air trapping chamber in which the sensing element 32 is situated.

The alcohol sensor 20 is positioned in the sensor casing 18, as shown in FIG. 2, so that the opening 33a of the cover 33 faces in a direction perpendicular to a flow line of an air flowing from the upstream opening 18a to a downstream opening 18b as shown by arrows in the figure.

Figure 4:
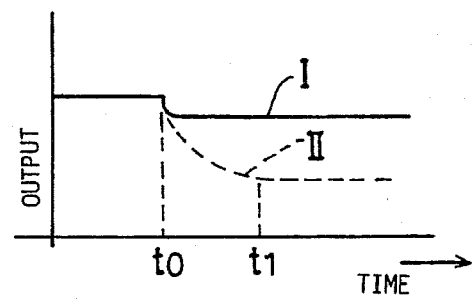
FIG. 4 is a graph showing a drift in an output of an alcohol sensor.

FIG. 4 is a graph of an output from the alcohol sensor 20. The suction pump 16 is driven at a time $t_0$ to suction air from the inlet 10a of the air passage 10 after the sensing element 32 is heated at a predetermined temperature. An air flow in the air trapping chamber of the alcohol sensor 20 is restricted in an arrangement of the alcohol sensor 20 shown in FIG. 1 since the air flow in the sensor casing 18 is blocked by the cover 33 and thus the sensing element 32 does not directly make contact with the air flow. Accordingly, a drift in temperature of the sensing element 32 is small as indicated by a line I of FIG. 4, and the temperature of the sensing element 32 reaches a constant level in a short time. Therefore, an accurate measurement of concentration of alcohol can be performed.

Figure 5:
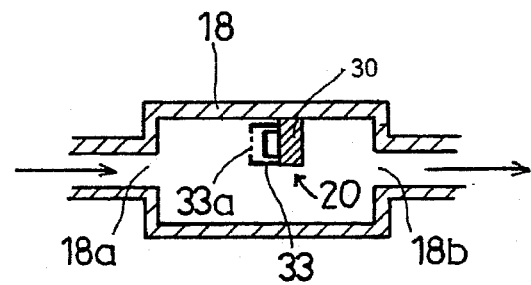
FIG. 5 is a cross sectional view of a sensor casing in which an alcohol sensor is arranged in a different way from an arrangement shown in FIG. 2.

On the other hand, if the opening 33a of the cover 33 of the alcohol sensor 20 faces toward the upstream opening 18a as shown in FIG. 5, the air flow enters through the opening 33a and directly hits the sensing element 32. This causes a large temperature drop of the sensing element 32, and thus a large drift of the output of the alcohol sensor 20 is generated as indicated by a dashed line II of FIG. 4. The output does not reach a constant level until a time $t_1$ shown in FIG. 4. The same output characteristic may be obtained in a case in which the cover 33 is removed from the alcohol sensor 20 arranged as shown in FIG. 1.

It should be noted that if the opening 33a faces toward the downstream opening 18b, the drift of the output of the alcohol sensor may be less than that indicated by the line I of FIG. 4. However, it takes a long time for the air suctioned from the inlet 10a of the air passage 10 to reach the sensing element 32a. Accordingly, a response time of the alcohol sensor 20 is increased, and thus this arrangement of the alcohol sensor 20 is not suitable for practical use.

Figure 6:
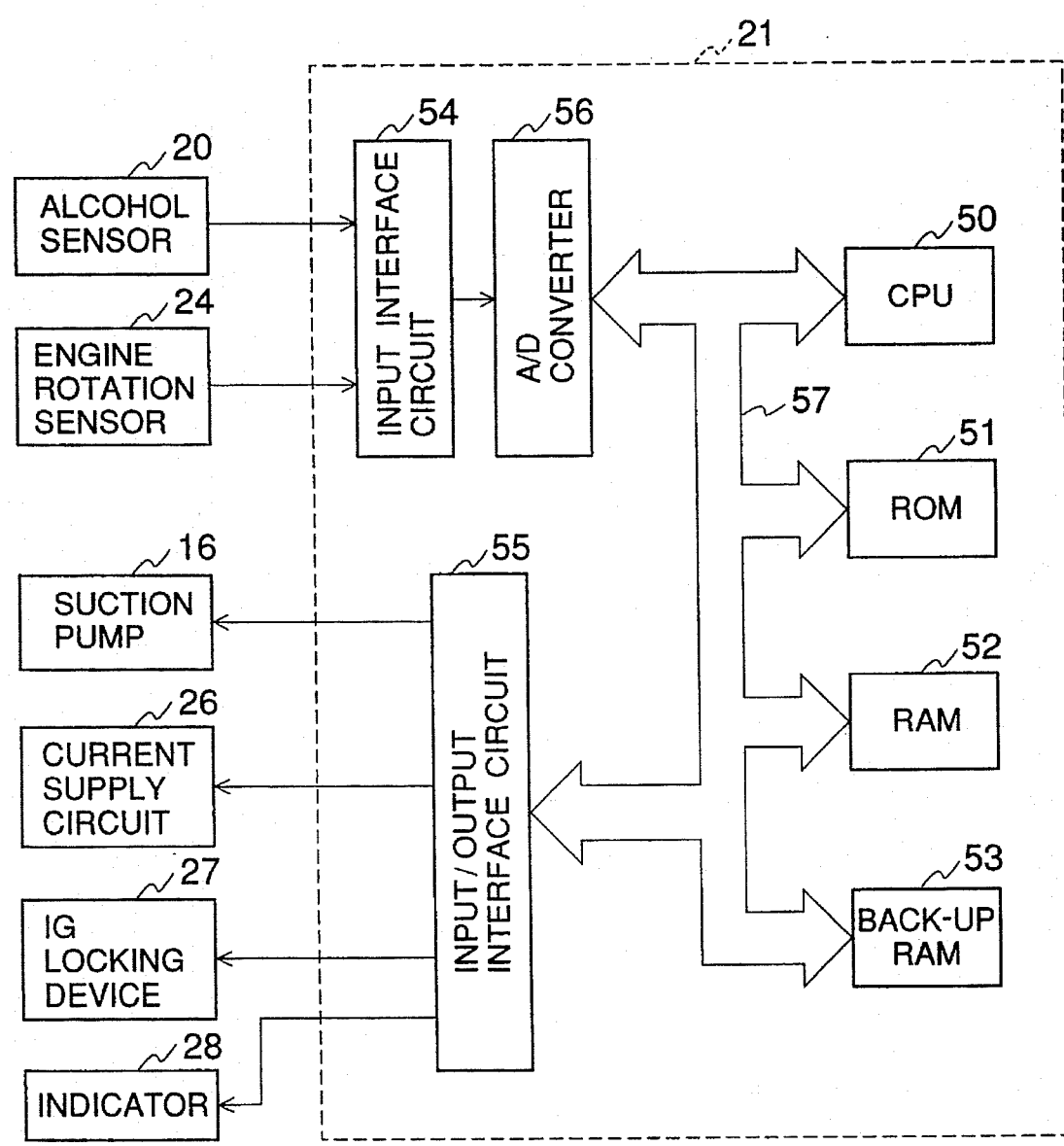
FIG. 6 is a block diagram of a controlling circuit shown in FIG. 1.

FIG. 6 is a block diagram of a controlling circuit 21 shown in FIG. 1. The controlling circuit 21 comprises a central processing unit (CPU) 50, a read only memory (ROM) 51, a random access memory (RAM) 52, a backup RAM 53, an input interface circuit with a multiplexer 54, an input/output interface circuit 55 and an A/D converter 56. Those parts are interconnected via a bus 57. The ROM 51 stores a process program. The RAM 52 is used as a working area. The back-up RAM 53 is used for storing data after an engine is stopped.

The A/D converter 56 takes in an output signal of the alcohol sensor 20 and a position signal output from an engine rotation sensor 24 via the input interface circuit 54, and converts them into digital signals. The converted digital signals are, in turn, sent to the bus 57. The input/output interface circuit 55 selectively sends control signals to a current supply circuit 26, an ignition (IG) locking device 27 and an indicator 28 so as to control them. The current supply circuit 26 is provided for supplying a current to the suction pump 16 and the heater coil 31 of the alcohol sensor 20.

Figure 7:
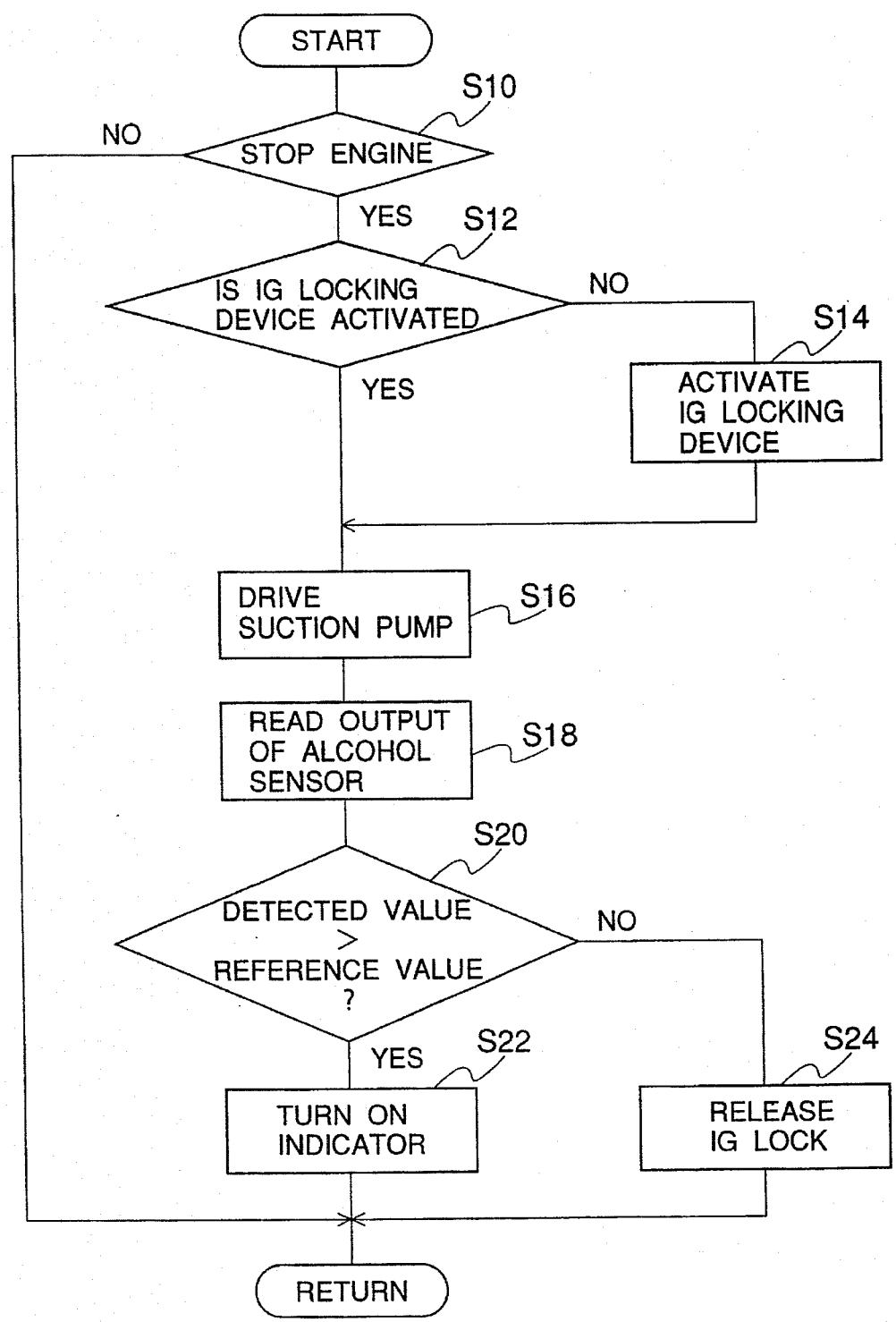
FIG. 7 is a flow chart of an operation performed by a controlling circuit shown in FIG. 1.

FIG. 7 is a flow chart of an operation performed by the controlling circuit 21. This routine starts when an accessory switch is turned on or when opening of a driver-side door is detected by a door sensor. After the routine is started, it is determined, in step 10 (hereinafter step is abbreviated as "S"), whether or not the engine is not in operation according to the output of the engine rotation sensor 24. If the engine is not in operation, the routine proceeds to S12 where it is determined whether or not the IG locking device 27 is activated. If it is determined that the engine is operated, the routine ends.

If it is determined, in S12, that the IG locking device is not activated, the routine proceeds to S14 to activate the IG locking device 27, and then proceeds to S16. If it is determined that the IG locking device is activated, the routine directly proceeds to S16 where the suction pump 16 is driven. After the suction pump is operated, the output signal of the alcohol sensor is read in S18, and the routine proceeds to S20.

It is determined, in S20, whether or not a concentration value of alcohol determined by the output signal of the alcohol sensor 20 is grater than a predetermined reference value. If the concentration value is greater than the reference value, the indicator is turned on in S22, and then the routine ends. If the concentration value is not greater than the reference value, the routine proceeds to S24 where the IG locking device 27 is deactivated, and then the routine ends.

It should be noted that when the IG locking device 27 is activated, an ignition key of a vehicle cannot be turned to an ignition position. Accordingly, the engine cannot be started, and thus drunken driving is prevented.

A description will now be given of a second embodiment of an alcohol measuring apparatus according to the present invention.

Figure 8:
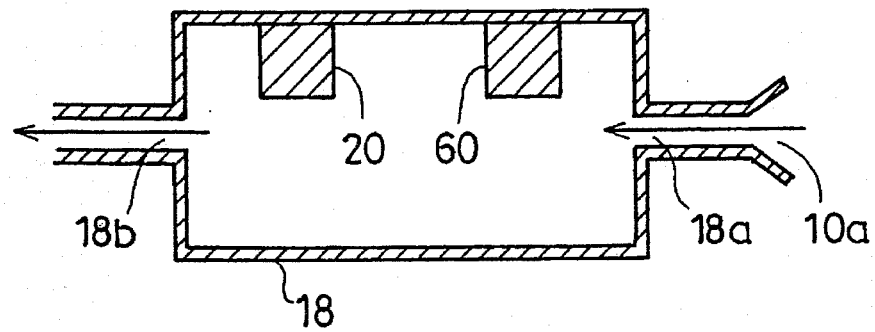
FIG. 8 is a cross sectional view of an essential part of a second embodiment according to the present invention.

FIG. 8 is a cross sectional view of the sensor casing which is an essential part of the second embodiment according to the present invention. In the second embodiment, the alcohol sensor 20 is attached on the top plate of the sensor casing 18 near the downstream opening 18b, and a humidity sensor 60 is attached on the top plate of the casing 18 near the upstream opening 18a. That is, the alcohol sensor 20 is located at a position downstream of the air flow in the sensor casing 18. The humidity sensor is provided for sensing water vapor contained in the air passing through the sensor casing 18. When a concentration value of water vapor sensed by the humidity sensor 60 exceeds a predetermined value, it is determined that an exhalation of a driver is suctioned into the alcohol measuring apparatus, and thus an accurate measurement of alcohol contained in the exhalation of the driver can be performed.

As shown in FIG. 8, the humidity sensor 60 is located at a position upstream-side of the alcohol sensor 20. Accordingly, an air heated by the alcohol sensor is directly flows out from the downstream opening of the sensor casing 18, and thus the heated air does not affect the characteristics of the humidity sensor 60. Therefore, decrease in accuracy of measurement performed by the alcohol measuring apparatus is prevented.

Figure 9A:
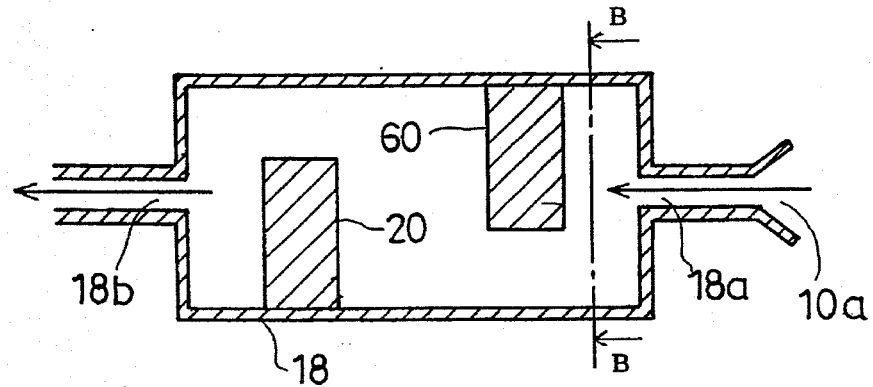
FIG. 9A is a cross sectional view of an essential part of a third embodiment according to the present invention.
Figure 9B:
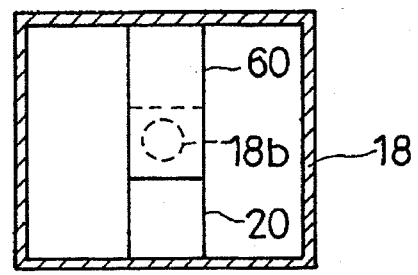
FIG. 9B is a cross sectional view taken along a line B—B of FIG. 9A.

FIG. 9A is a cross sectional view of the sensor casing 18 which is an essential part of a third embodiment according to the present invention, and FIG. 9B is a cross sectional view taken along a line B—B of FIG. 9A.

In the third embodiment, the alcohol sensor 20 is attached on the bottom plate of the sensor casing 18 near the downstream opening 18b, and a humidity sensor 60 is attached on a top plate of the sensor casing 18 near the upstream opening 18b.

According to this arrangement of the sensors 20 and 60, the air flowing in the sensor casing 18 is agitated by the humidity sensor 60 and then agitated by the alcohol sensor 20. Accordingly, concentration of alcohol and water vapor contained in the air flowing through the sensor casing 18 becomes uniform, which results in an improvement of measurement accuracy.

It should be noted that a sensor for sensing another component, such as methyl mercaptan, contained in an exhalation may be added in the sensor casing 18. Additionally, a protrusion or a groove may be formed in the sensor casing so as to agitate the air passing through the sensor casing 18.

Figure 10:
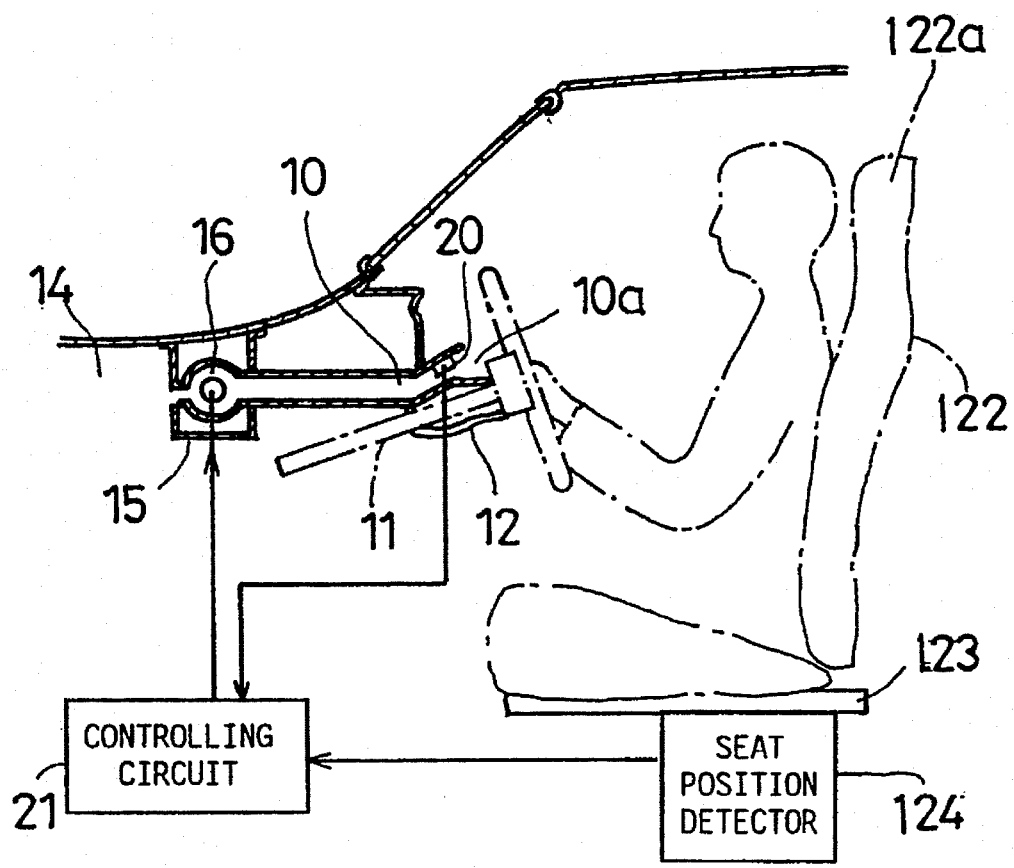
FIG. 10 is an illustration of a fourth embodiment of an alcohol measuring apparatus according to the present invention.

A description will now be given, with reference to FIG. 10, of a fourth embodiment according to the present invention. FIG. 10 is an illustration of the fourth embodiment of an alcohol measuring apparatus according to the present invention. In FIG. 10, parts that are the same as the parts shown in FIG. 1 are given the same reference numerals, and descriptions thereof will be omitted.

The basic structure of the fourth embodiment is the same as that of the first embodiment shown in FIG. 1. In addition to the parts of the first embodiment, the fourth embodiment is provided with a seat position detector 124 as means for detecting a position of a driver's seat 122. The seat position detector 124 is provided on a seat sliding mechanism 123 of the driver's seat 122. The seat position detector 124 outputs a voltage signal corresponding to a position of the driver's seat 122, and sends it to the controlling circuit 21.

Figure 11:
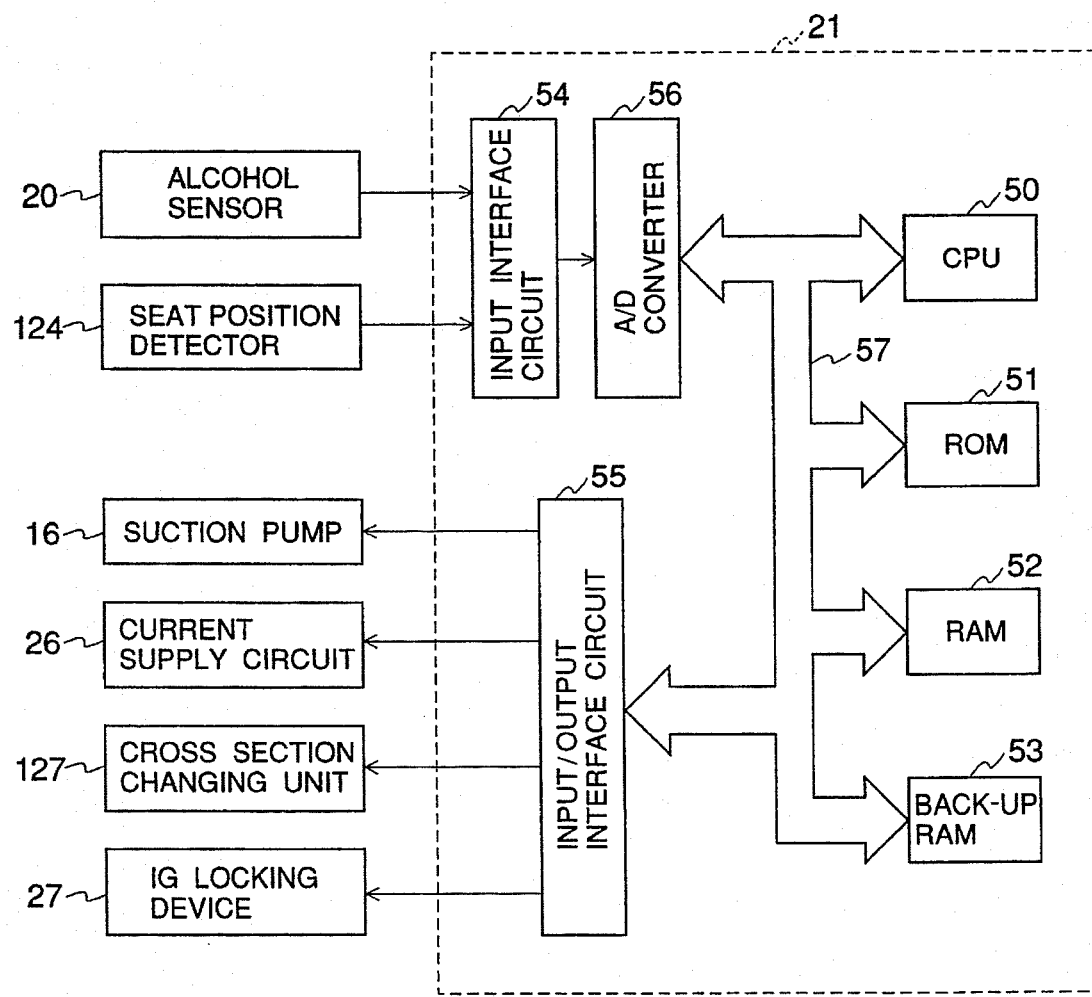
FIG. 11 is a block diagram of a controlling circuit shown in FIG. 10.

FIG. 11 is a block diagram of the controlling circuit 21 shown in FIG. 10. In FIG. 11 parts that are the same as the parts shown in FIG. 6 are given the same reference numerals, and descriptions thereof will be omitted.

The A/D converter 56 takes in an output signal of the alcohol sensor 20 and a position signal output from a seat position detector 124 via the input interface circuit 54, and converts them into digital signals. The converted digital signals are, in turn, sent to the bus 57. The input/output interface circuit 55 selectively sends control signals to a current supply circuit 26, an ignition (IG) locking device 27 and a cross section changing unit 127 (described later) so as to control them. The current supply circuit 26 is provided for supplying a current to the suction pump 16 and the heater coil 31 of the alcohol sensor 20.

Figure 12:
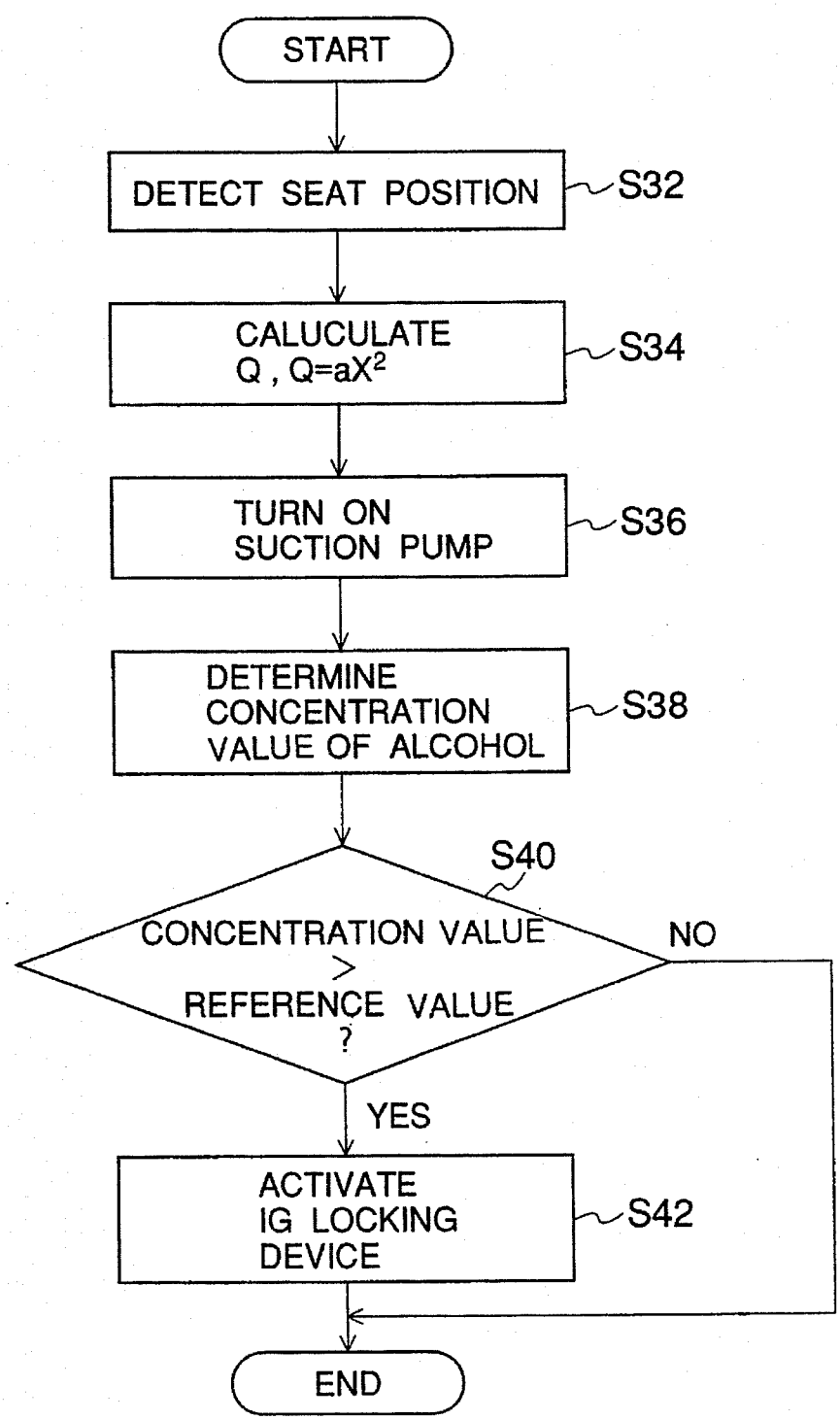
FIG. 12 is a flow chart of an operation performed by a controlling circuit shown in FIG. 10.

FIG. 12 is a flow chart of an operation performed by the controlling circuit 21 shown in FIG. 10.

When the routine of the operation is started, the position signal is taken in, in S32, so as to detect a current position of the driver's seat 122, and then an amount Q (l/min) of air flow suctioned by the suction pump 16 is calculated, in S34, in accordance with the following equation.

$Q = aX^2$ where a is a predetermined factor; and

X is a distance (cm) from a pillow 122a of the driver's seat 122 to the end 10a of the air passage 10.

In S36, a performance of the suction pump 16 is controlled so that an amount of air suctioned is equal to the calculated value Q, and the routine proceeds to S38 where a concentration value of alcohol is determined in accordance with the output signal of the alcohol sensor 20.

It is determined, in S40, whether or not the determined concentration value of alcohol is greater than a predetermined reference value. If it is determined that the concentration value is greater than the reference value, the routine proceeds to S42 where the IG locking device 27 is activated, and then the routine ends. Otherwise the routine ends without activating the IG locking device 27.

In the present embodiment, since a suction amount of the suction pump is controlled in accordance with a square of the distance X between the pillow 122a of the driver's seat 122 and the end 10a of the air passage 10, a constant amount of an exhalation of the driver can be always suctioned into the measuring apparatus. Accordingly, an accurate measurement of alcohol contained in the exhalation of the driver can be performed.

Figure 13:
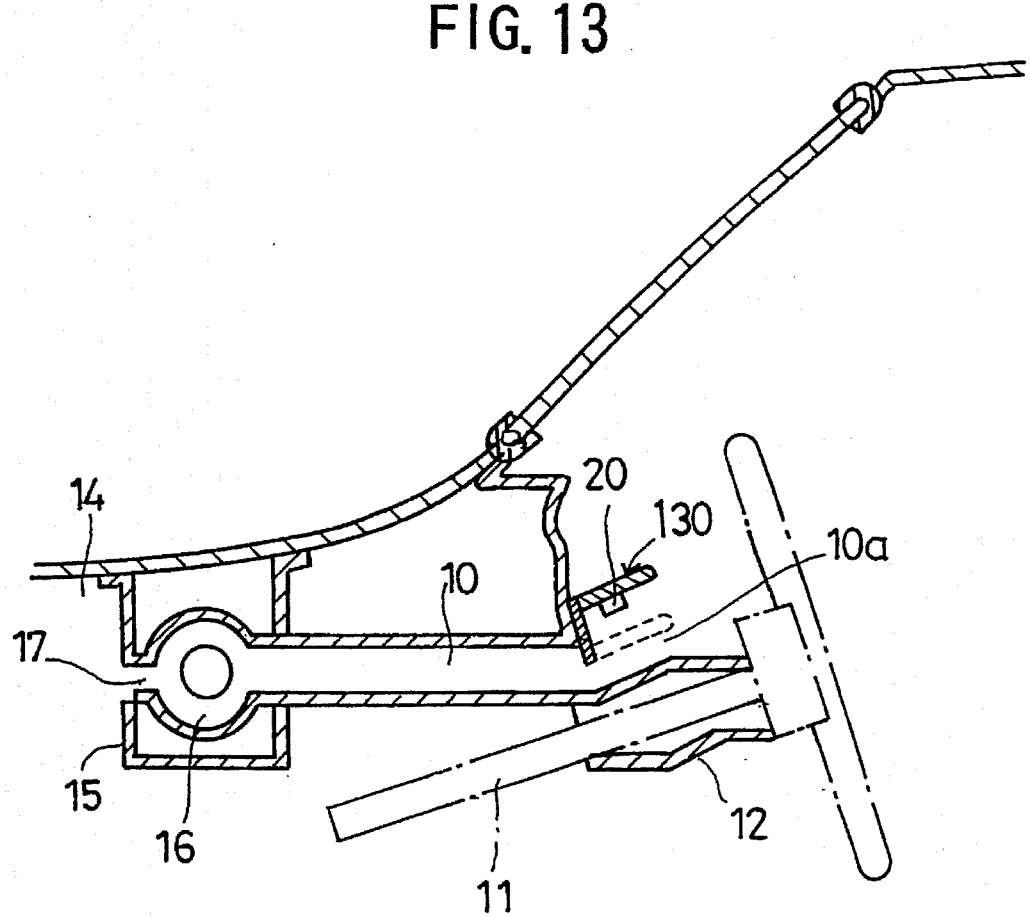
FIG. 13 is an illustration of an essential part of a fifth embodiment according to the present invention.

A description will now be given of a fifth embodiment according to the present invention. FIG. 13 is an illustration of an essential part of the fifth embodiment according to the present invention. Other parts are the same as that of the fourth embodiment. As shown in FIG. 13, a cross section changing mechanism 130 is provided on the inlet 10a of the air passage 10.

Figure 14A:
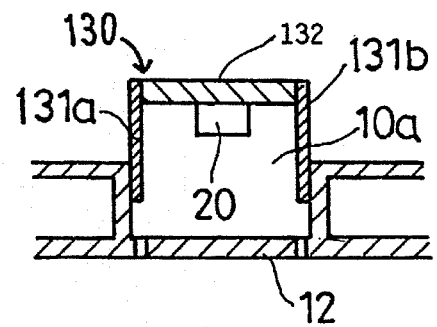
FIG. 14A is a cross sectional view of a cross section changing mechanism shown in FIG. 13.
Figure 14B:
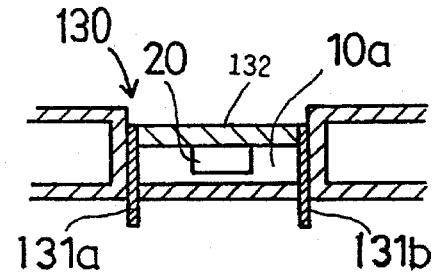
FIG. 14B is a cross sectional view of a cross section changing mechanism shown in FIG. 13.

The cross section changing mechanism 130 comprises, as shown in FIGS. 14A and 14b, legs 131a and 131b and a moving plate 132. The alcohol sensor 20 is attached on the moving plate 132 of the cross section changing mechanism 130. The legs 131a and 131b are inserted into holes formed on the cover 12 of the steering column 11. The moving plate 132 is moved by means of the cross section changing unit 127 such as a solenoid plunger so that a cross section area of the inlet 10a of the air passage 10 is varied by a signal from the controlling circuit 21.

Figure 15:
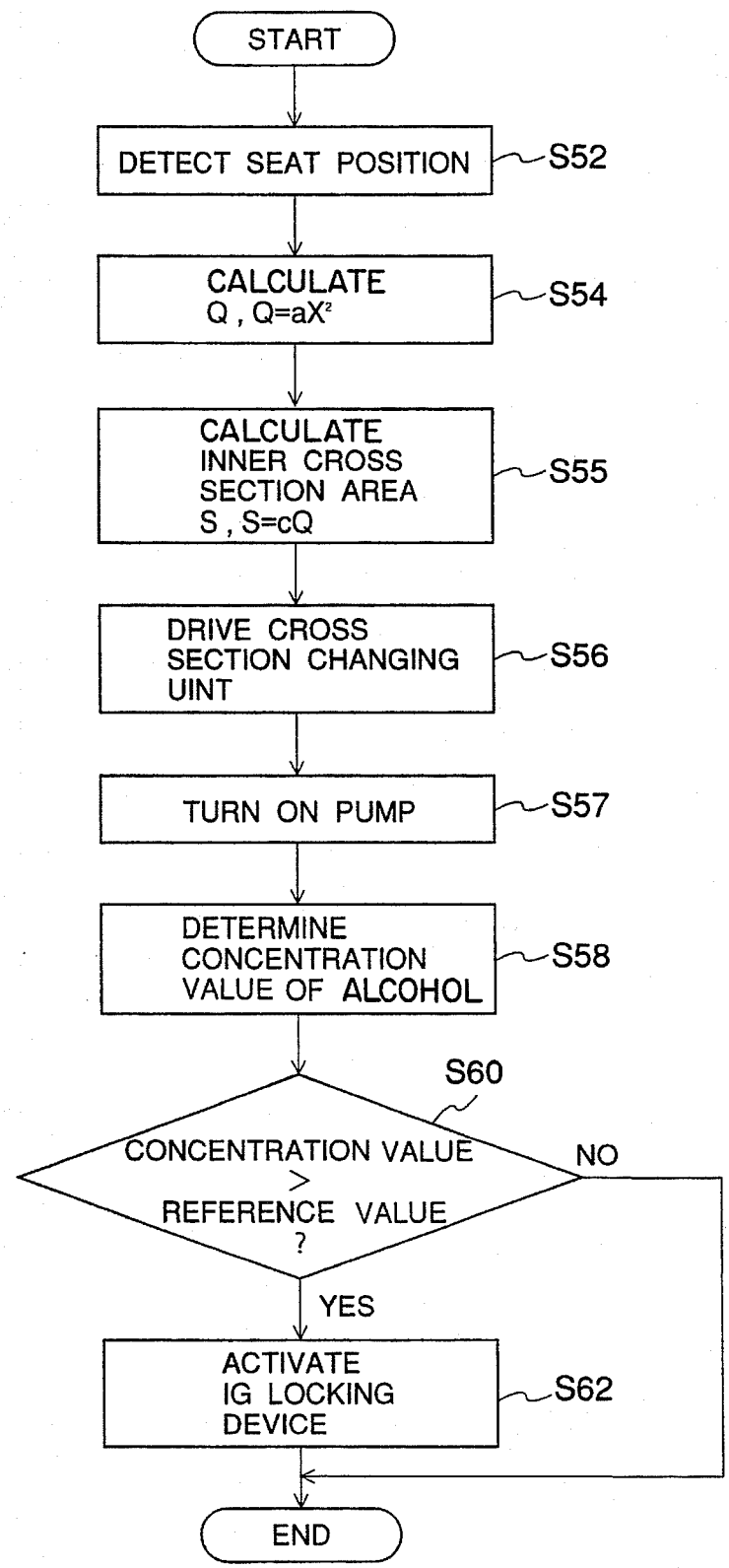
FIG. 15 is a flow chart of an operation performed by a controlling circuit of a fifth embodiment.

FIG. 15 is a flow chart of an operation of the fifth embodiment according to the present invention.

When the routine of the operation is started, the position signal is taken in, in S52, so as to detect a current position of the driver's seat 122, and then an amount Q (l/min) of air flow suctioned by the suction pump 16 is calculated, in S54, similarly to the above-mentioned fourth embodiment.

In S55, an inner cross section area S of the inlet 10a of the air passage 10 is calculated in accordance with the following equation.

$$S = cQ$$

where c is a predetermined constant.

For example, when X=50 cm, Q=1 l/min and S=5 cm$^2$, and when X=80 cm, Q=2.5 l/min and S=12.5 cm$^2$.

After that, the cross section changing unit 127 is driven, in S56, so that the inner cross section area of the inlet 10a becomes S.

In S57, a performance of the suction pump 16 is controlled so that an amount of air suctioned is equal to the calculated value Q, and the routine proceeds to S58 where a concentration value of alcohol is determined in accordance with the output signal of the alcohol sensor 20.

It is determined, in S60, whether or not the determined concentration value of alcohol is greater than a predetermined reference value. If it is determined that the concentration value is greater than the reference value, the routine proceeds to S62 where the IG locking device 27 is activated, and then the routine ends. Otherwise the routine ends without activating the IG locking device 27.

In the present embodiment, the inner cross section area is regulated by means of the cross area changing unit 127 and the moving plate 132 so that a constant air flow velocity can be always obtained around the alcohol sensor 20 regardless of the suction amount of the suction pump 16. Accordingly, an accurate measurement of alcohol contained in the exhalation of the driver can be performed.

Figure 16:
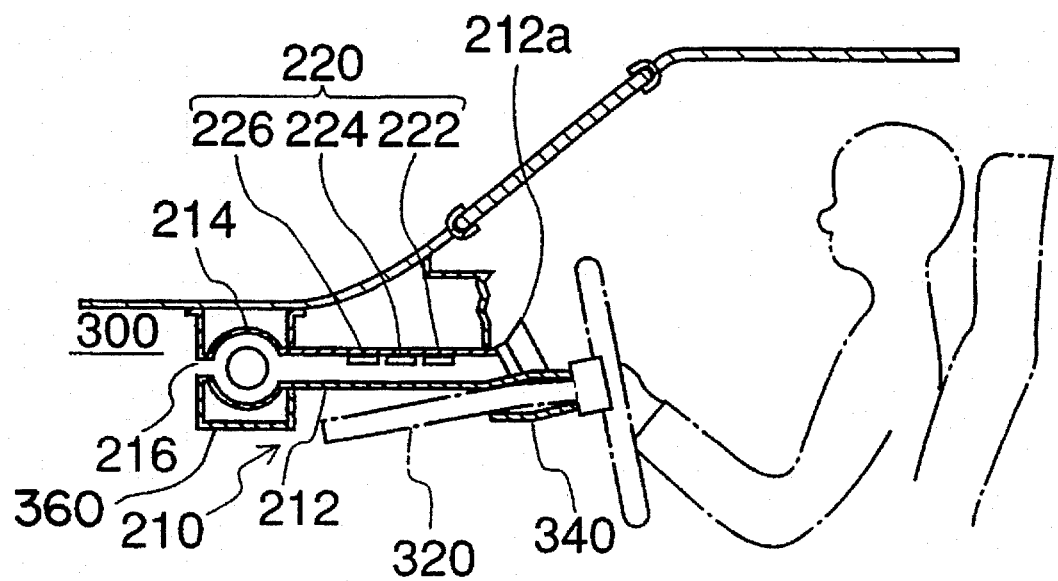
FIG. 16 is an illustration of a sixth embodiment of a measuring apparatus according to the present invention.

A description will now be given of a sixth embodiment of a measuring apparatus for alcohol according to the present invention. FIG. 16 is an illustration of the first embodiment according to the present invention. The first embodiment according to the present invention is a measuring apparatus for measuring alcohol contained in an exhalation of a driver of a vehicle. The measuring apparatus is provided in the vehicle near the driver.

The measuring apparatus comprises a suction unit 210 and an attaching unit 360. The suction unit 210 comprises a air passage 212 and a suction pump 214 located in the attaching unit 360. An inlet at one end of the air passage 212 is fixed on a cover 340 of a steering column 320, and provided with a horn-like opening 212a so as to effectively collect an exhalation of the driver. The other end of the air passage 212 is inserted into the attaching unit 360 attached in an engine compartment 300.

The suction pump 214 is located inside the attaching unit 160. A mixture of exhalation and air suctioned into the suction unit 210 is exhausted from an exhaust port 216 formed on a wall of the attaching unit 360 via the suction pump 214.

A sensor attaching portion 220 is provided near a center of the air passage 212. In the sensor attaching portion 220, an alcohol sensor 222, a humidity sensor 224 and a sulfide sensor 226 are arranged in a predetermined positional relationship.

The alcohol sensor 222 is provided for measuring alcohol component contained in a mixture of exhalation and surrounding air suctioned into the air passage 212. As the alcohol sensor, for example, a sensor comprising an oxide semiconductor such as tin oxide is used. One of the commercially available alcohol sensor is the sensor designated TGS822 manufactured by FIGARO Engineering Inc.

The humidity sensor 224 is provided for sensing water vapor contained in the mixture of exhalation and the surrounding air suctioned into the air passage 212. As a humidity sensor, for example, a sensor comprising a polymer membrane may be used. This humidity sensor senses a change in capacitance of the polymer membrane. One of the commercially available humidity sensors is the capacitance change type humidity sensor manufactured by VAISALA.

Figure 18:
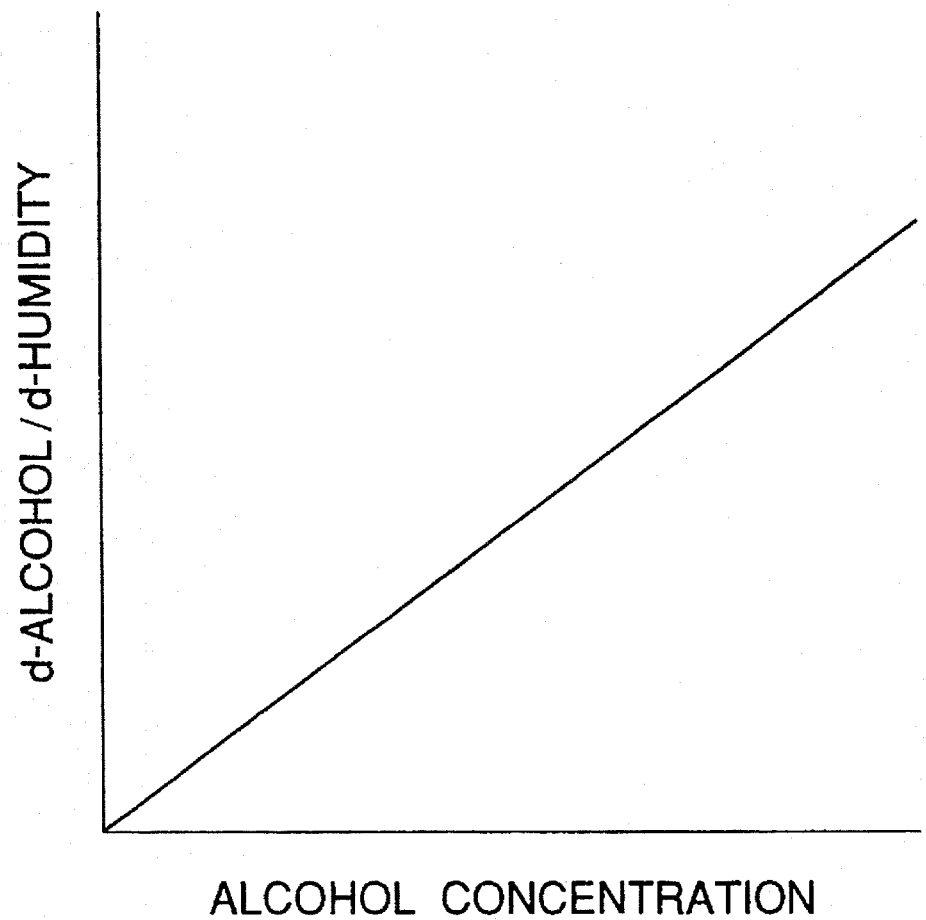
FIG. 18 is a graph showing a relationship between concentration of alcohol in an oral cavity and a ratio of the increment of an output of an alcohol sensor to that of a humidity sensor.

The humidity sensor 224 is used for correcting an effect of a variation in an amount of an exhalation suctioned into the measuring apparatus. That is, using concentration of water vapor contained in the exhalation is suitable for correcting the variation in an amount of the exhalation. An amount of water vapor contained in an exhalation is constant, and this amount corresponds to a saturated vapor pressure at 34° C. Accordingly, concentration of alcohol in an oral cavity is proportional to a ratio of the concentration of the alcohol to the concentration of water vapor in the oral cavity. As shown in FIG. 18, it is assumed that this ratio does not change when the exhalation is diluted in the air, and is represented by a ratio of the increment of an output of the alcohol sensor 222 (d-alcohol) to that of an output of the humidity sensor 224 (d-humidity).

Accordingly, concentration of alcohol in the oral cavity can be assumed using the relationship shown in a line of FIG. 18. An inclination of the line shown in FIG. 18 corresponds to a reciprocal of the concentration of water vapor in the oral cavity. Using, for example, a saturated water vapor pressure at 34° C. (39.9 mmHg) as the concentration of water vapor in the oral cavity, the inclination is represented by 1/39.9.

As mentioned above, an exact concentration of alcohol can be obtained as a function of d-alcohol/d-humidity in accordance with concentration of alcohol and humidity of the exhalation suctioned in the measuring apparatus regardless of the variation in amount of the exhalation suctioned in the measuring apparatus. It should be noted that although there are other factors which may affect the humidity, the above-mentioned method assures to eliminate the problem caused by putting a wet hand over the opening of the air passage because the object to be measured is only air determined by means of the sulfide sensor to be an exhalation.

The sulfide sensor 226 is provided for sensing methyl mercaptan contained in the mixture of exhalation and the surrounding air suctioned into the air passage 12. As a sulfide sensor, for example, a sensor comprising an oxide semiconductor such as tin oxide is used. This sulfide sensor senses a change in resistance of oxide semiconductor due to oxidation of the sulfide such as the methyl mercaptan. It should be noted that the methyl mercaptan, which is a kind of sulfide, is known as one of the main component of smell of breath. Accordingly, existence of an exhalation can be determined by sensing the methyl mercaptan. One of the commercially available sulfide sensors suitable for the present invention is a sensor designated TGS825 manufactured by FIGARO Engineering Inc.

Preferably, at least one of the alcohol sensor 222, humidity sensor 224 and sulfide sensor 226 is covered with a porous cellulose membrane (thickness: 100 μm, inner diameter of each hole: 0.1 μm) which delays a diffusion of the exhalation toward the sensor. The diffusion characteristic of the cellulose membrane for the sensor is determined to equalize each response time to the detected component of these sensors. The three sensors are preferably arranged close to each other so that exhalation reaches to each of the sensors at the same time.

The equalization of the response time of each of the sensors contributes to an improvement of a measuring accuracy and reduction of measuring time. In a determination of the alcohol concentration, for example, a determination using a value of the ratio of changes in the output from the two sensors when it reaches to a stable level (indicated by a time B of FIG. 19-(c)) is much faster than that using values of the outputs from the two sensors when they reached a stable level (indicated by a time A of FIG. 19-(a) and (b)). In order to use the ratio of changes in the output from the two sensors, it is preferable to set the response time of each of the sensors to the same value. The same method may be applied to a measurement of concentration of sulfide using the sulfide.

Figure 17:
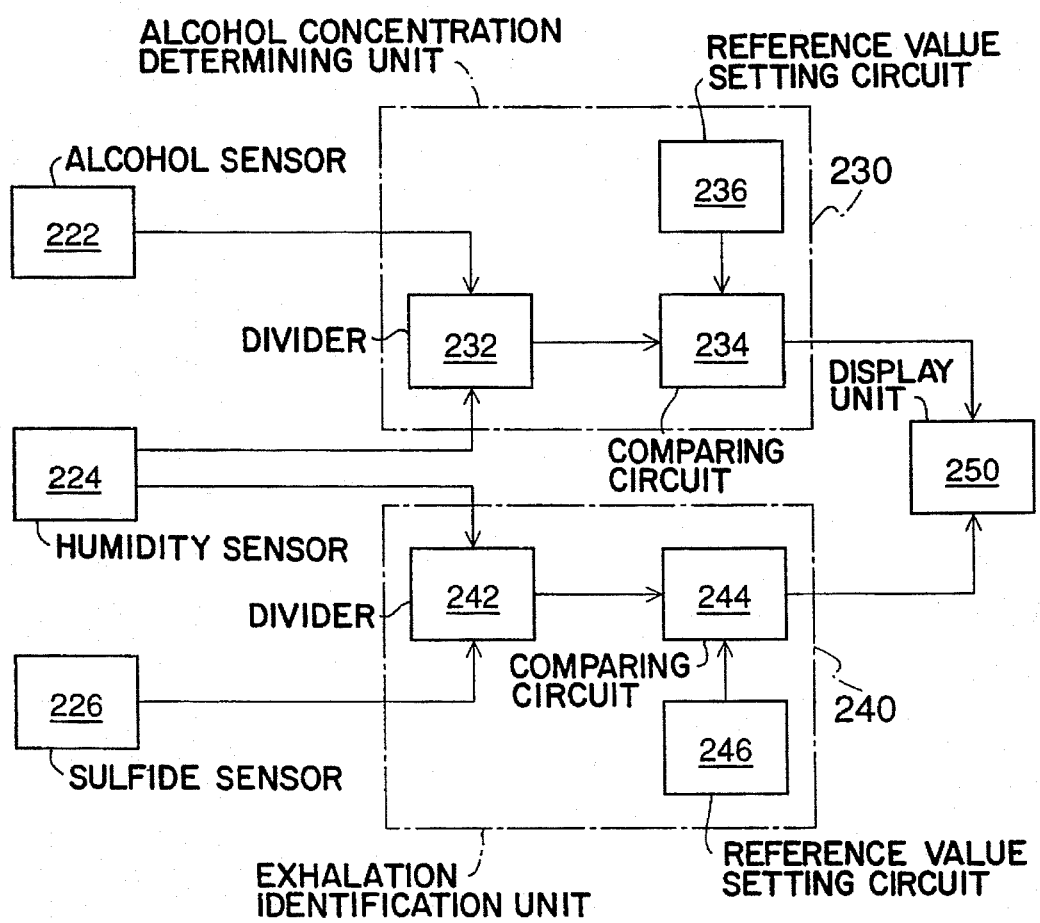
FIG. 17 is a block diagram of a detecting circuit provided in the measuring apparatus shown in FIG. 16.

FIG. 17 is a block diagram of a detecting circuit provided in the sixth embodiment according to the present invention. Outputs from the alcohol sensor 222 and the humidity sensor 224 are supplied to an alcohol concentration determining unit 230. Outputs from the humidity sensor 224 and the sulfide sensor 226 are supplied to an exhalation identification unit 240.

The alcohol concentration determining unit 230 comprises a divider 232, a comparing circuit 234 and a reference value setting circuit 236. The divider 232 calculates a ratio of the increment of an output of the alcohol sensor 222 (d-alcohol) to that of an output of the humidity sensor 224 (d-humidity), and outputs a result to the comparing circuit 234 as a voltage signal.

The reference value setting circuit 236 provides a reference value used for setting an alcohol concentration to be detected. For instance, when an alcohol concentration value of 120 ppm is given as an indication of a drunken driver, the reference value setting circuit 236 outputs a predetermined voltage signal corresponding the alcohol concentration value of 120 ppm.

The comparing circuit 234 compares the voltage signal output from the reference value setting circuit 236 with the voltage signal output from the divider 232, and a result of comparison is output to a display unit 250. For example, if the voltage signal output from the reference value setting circuit 236 is less than the voltage signal output from the divider 232, the comparing circuit 234 outputs a low (L) level voltage signal. If the voltage signal output from the reference value setting circuit 236 is greater than the voltage signal output from the divider 232, the comparing circuit 234 outputs a high (H) level voltage signal.

The exhalation identification unit 240 comprises a divider 242, a comparing circuit 244 and a reference value setting circuit 246. The divider 242 calculates a ratio of the increment of an output of the sulfide sensor 226 (d-sulfide) to that of an output of the humidity sensor 224 (d-humidity), and outputs a result to the comparing circuit as a voltage signal.

The reference value setting circuit 246 provides a reference value used for determining a presence of an exhalation. For instance, when methyl mercaptan concentration value of $0.1_{ppm}$ is given as an indication of presence of an exhalation, the reference value setting circuit 246 outputs a predetermined voltage signal corresponding the methyl mercaptan concentration value of $0.1_{ppm}$.

The comparing circuit 244 compares the voltage signal output from the reference value setting circuit 246 with the voltage signal output from the divider 242, and a result of comparison is output to the display unit 250. For example, if the voltage signal output from the reference value setting circuit 246 is less than the voltage signal output from the divider 242, the comparing circuit 244 outputs a high (H) level voltage signal. If the voltage signal output from the reference value setting circuit 246 is greater than the voltage signal output from the divider 242, the comparing circuit 244 outputs a low (L) level voltage signal.

The display unit 250 notifies the driver a status of an operation of the alcohol measuring apparatus and a determination of concentration of the alcohol contained in an exhalation. For example, when the voltage signal output from the exhalation identification unit 240 is at the L level, the display unit 250 notify the driver by means of display that the measuring apparatus is in a waiting state for exhalation. When the voltage signal is at the H level, it is displayed that the measuring apparatus is in a measuring process.

Additionally, when the voltage signal output from the exhalation identification unit 240 is at the high level, and when the voltage signal output from the alcohol concentration determining unit 230 is at the L level, the display unit 250 displays that the driver is at a drunken driving level. When the voltage signal output from the alcohol concentration determining unit 230 is at the H level, the display unit 250 displays that the driver is at a normal level with respect to alcohol.

Figure 20:
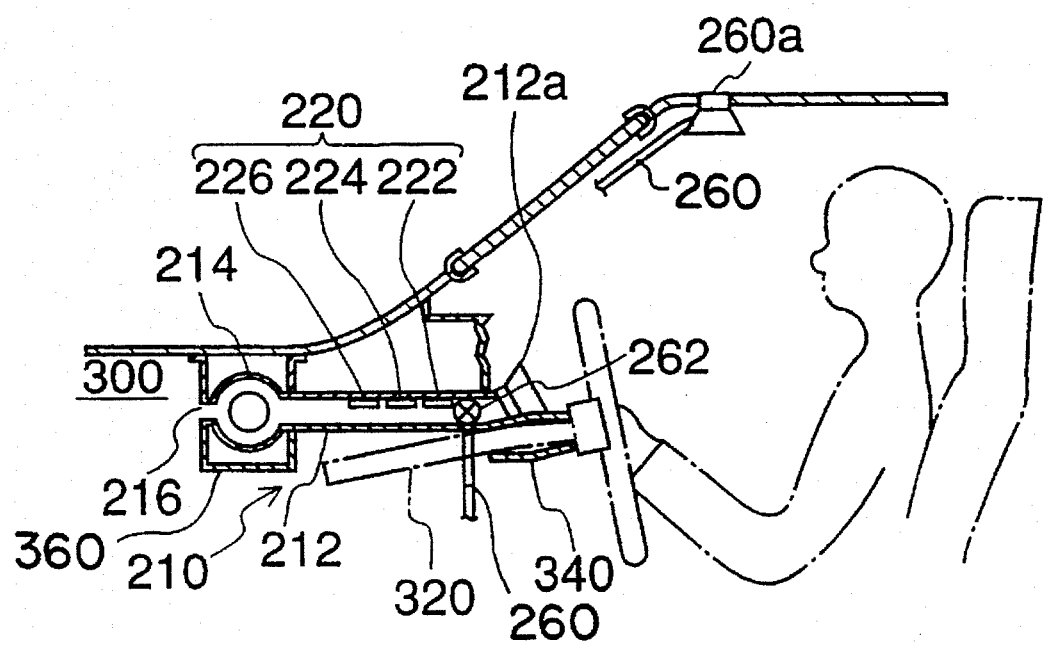
FIG. 20 is an illustration of a seventh embodiment of a measuring apparatus according to the present invention.

A description will now be given, with reference to FIG. 20, of a seventh embodiment according to the present invention. In FIG. 20, parts that are the same as the parts shown in FIG. 16 are given the same reference numerals, and description thereof will be omitted.

As shown in FIG. 20, the seventh embodiment differs from the above-mentioned sixth embodiment in that a second opening 260a is additionally provided at a position remote from the opening 212a (a first opening). The second opening 260a communicates with the air passage 212 via an air passage 260. The second opening 260a is located at a position near the driver, but where little exhalation is sectioned. In the present embodiment, the second opening 260a is attached at a position slightly ahead of the driver on a roof header. The air passage 260 goes through the inner space of the roof header, inner space of a right front-pillar and then an inner space of a bottom portion of an instrument panel. An end of the air passage 260 is connected to the air passage 212 between the sensor attaching portion 220 and the opening 212a via a 3-way valve 262.

Figure 21:
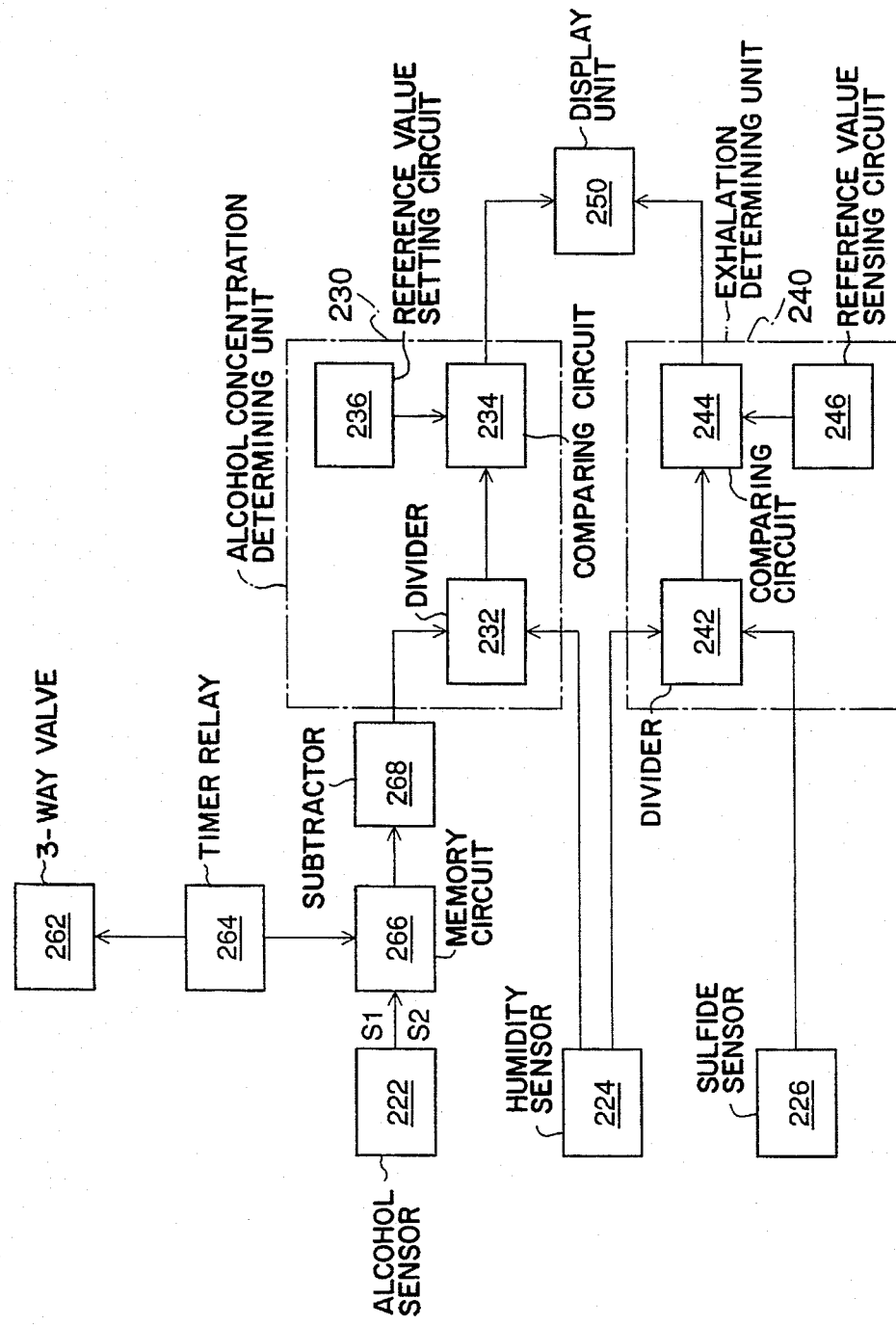
FIG. 21 is a block diagram of a detecting circuit provided in the measuring apparatus shown in FIG. 20.

FIG. 21 is a block diagram of a detecting circuit of the second embodiment.

The detecting circuit of the second embodiment differs from that of the first embodiment in that the detecting circuit of the second embodiment is additionally provided with a timer relay 264, a memory circuit 266 and a subtracter 268. The timer relay 264 controls switching of the 3-way valve 262. The memory circuit 266 stores an output signal from the alcohol sensor 222. An output of the memory circuit 266 is supplied to the subtracter 268.

The 3-way valve 262 is switched in accordance with an output signal of the timer relay 264 so that air is suctioned from either the first opening 212a or the second opening 260a. Accordingly, a detection signal S1 which corresponds to the alcohol concentration of the air suctioned from the first opening 212a and a detection signal S2 which corresponds to the alcohol concentration of the air suctioned from the second opening 260a are separately stored in accordance with the switching of the 3-way valve 262, and are output to the subtracter 268. The subtracter 268 calculates a difference between the signal S1 and the signal S2, and a result is output to the alcohol concentration determining unit 230. Structures and functions of the alcohol concentration determining unit 230, the exhalation identification unit 240 and the display unit 250 are the same as that of the first embodiment, and descriptions thereof will be omitted.

A description will now be given of advantages of the second embodiment according to the present invention.

Figure 22:
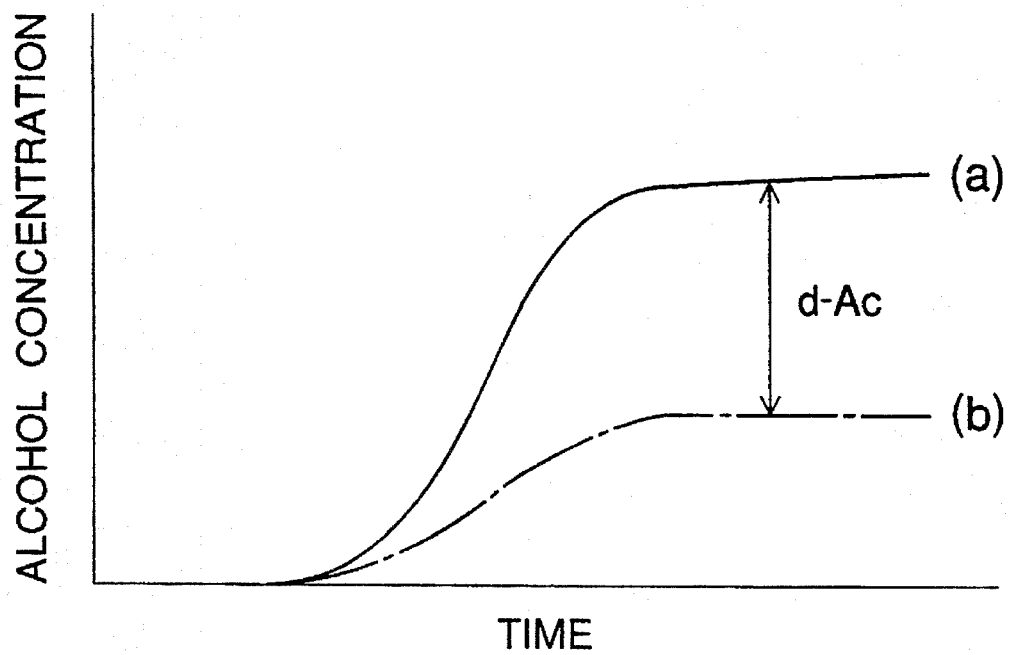
FIG. 22 is a graph showing alcohol concentration measured by an alcohol sensor provided in the measuring apparatus shown in FIG. 20.

In a case air is suctioned from the first opening 212a provided at a position where an exhalation of the driver is easily suctioned, alcohol contained in the exhalation and alcohol such as generated from hair tonic of the driver are simultaneously suctioned. Under such a condition, the detection signal output from the alcohol sensor 222 includes both alcohols as shown in FIG. 22. A solid line (a) of FIG. 22 indicates a change in concentration of alcohol sensed by the alcohol sensor 222 when air is suctioned from the first opening 212a, and a chain line (b) indicates that of air suctioned from the second opening 260a. A difference between the line (a) and the line (b) indicates a true concentration of the alcohol contained in the exhalation. The reason for this is that the exhalation of the driver is generally blown forwards, and thus most part of alcohol contained in the exhalation is suctioned only from the first opening 212a, while alcohol generated from the hair tonic reaches to both the first opening 212a and the second opening 260a by a natural diffusion, and then is suctioned from the both openings in the same amount.

In a case in which a person seating on the next seat to the driver contains alcohol, alcohol suctioned from each opening is almost the same because each of the openings is located distant from the person seating on the seat next to the driver.

Accordingly, by subtracting concentration of alcohol contained in the air suctioned from the second opening 260a from that of the air suctioned from the first opening 212a, a true concentration of the alcohol contained in the exhalation of the driver can be obtained. The true concentration of the alcohol contained in the exhalation is indicated by d-Ac in FIG. 22. Thus, alcohol contained in an exhalation of the driver can be measured in a high accuracy.

In the above-mentioned first and second embodiments, it is preferred to provided warning means or means for disabling an operation of the vehicle when the driver is determined to be in a drunken condition. The warning means may comprise a buzzer. The means for disabling the operation of the vehicle may be achieved by 10 means of an ignition interlock or a shift-lever interlock.

Figure 23:
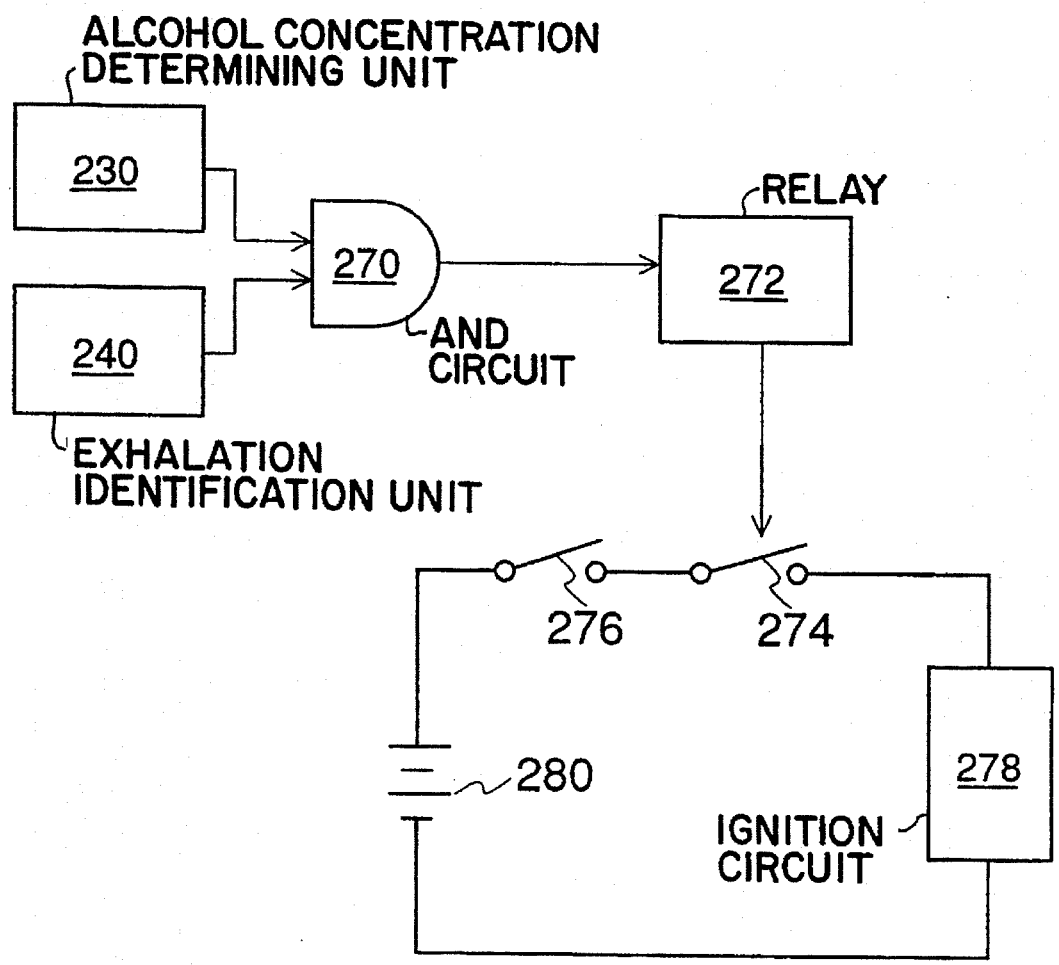
FIG. 23 is a circuit diagram of a controlling circuit for an ignition interlock.

FIG. 23 is a circuit diagram of a controlling circuit for the ignition interlock. In this controlling circuit, the outputs from the alcohol concentration determining unit 230 and the exhalation identification unit 240 are supplied to an AND circuit 270. An output from the AND circuit 270 is supplied to a relay 272. The relay 272 is connected to a normally open OK switch 274 which is provided for activating an ignition circuit 278. On/off of the OK switch 274 is controlled by the relay 272. In FIG. 23, a label 276 indicates a main switch, and a label 280 indicates a battery.

In the above-mentioned structure, the ignition circuit 278 is not operable by only turning on the main switch 276 because the OK switch 274 is open. That is, only when the outputs from the alcohol concentration determining unit 230 and the exhalation identification unit 240 are at the H level, the OK switch is closed by means of the relay 272, and thus the ignition circuit becomes operable to start an engine of the vehicle.

Figure 24:
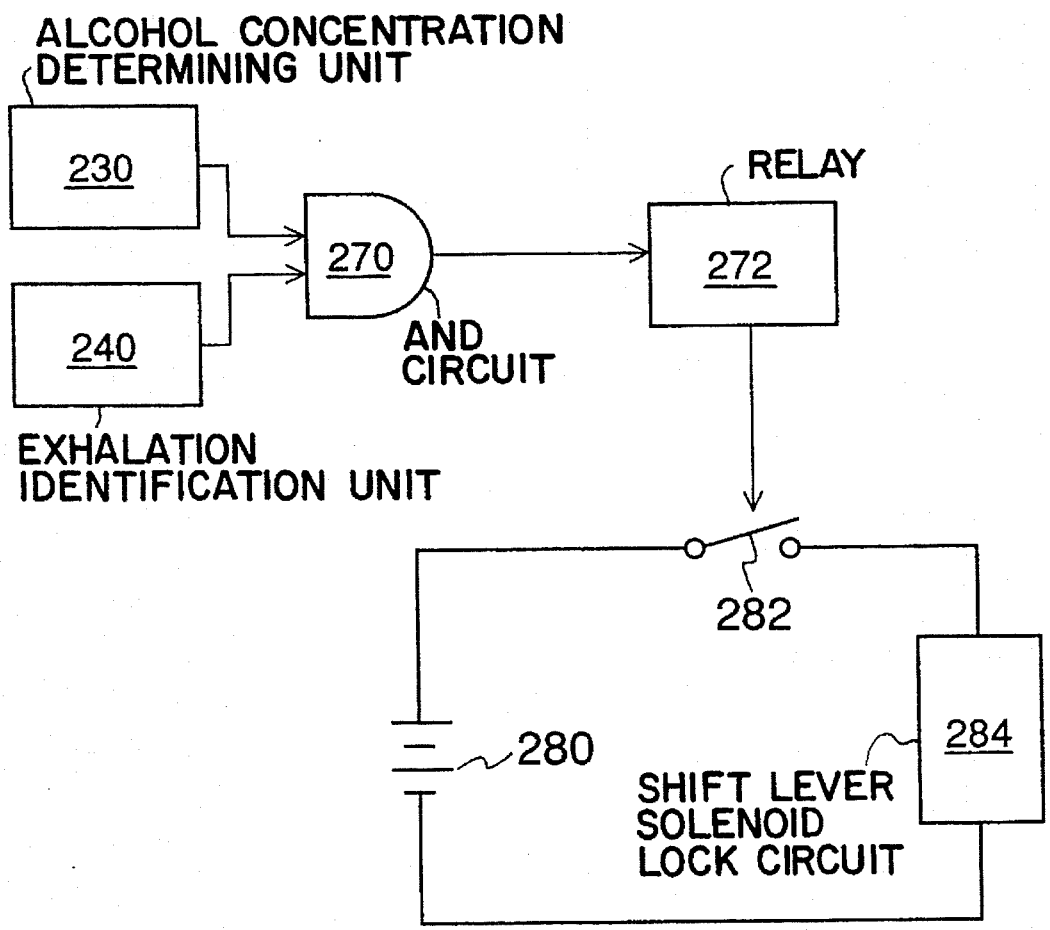
FIG. 24 is a circuit diagram of a controlling circuit for a shift lever interlock.

FIG. 24 is a circuit diagram of a controlling circuit for the shift-lever interlock. In this controlling circuit, the relay 272 is connected to a solenoid lock switch 282 which is provided for activating a shift lever solenoid lock circuit 284. By having this controlling circuit, the engine can be started, but a shift lever cannot be operated due to a function of the solenoid lock switch 282. The solenoid lock switch 282 is opened only when the outputs from the alcohol concentration determining unit 230 and the exhalation identification unit 240 are at the H level, and thus the shift lever solenoid lock switch 284 becomes inactive resulting the shift lever to be in an operable condition.

The present invention is not limited to the specifically disclosed embodiments, and variations and modifications may be made without departing from the scope of the present invention.

What is claimed is:

1. An alcohol measuring apparatus for measuring a concentration of alcohol contained in an exhalation, the alcohol measuring apparatus comprising:

a suction unit having an air passage for introducing a mixture of air and exhalation, and suction means connected to said air passage for suctioning the mixture;

a sulfide sensor, provided in said air passage upstream of said suction means, for sensing a sulfide contained in the mixture;

a humidity sensor, provided in said air passage upstream of said suction means, for sensing water vapor contained in the mixture;

an alcohol sensor, provided in said air passage upstream of said suction means, for sensing alcohol contained in the mixture;

an exhalation identification unit for determining a presence of the exhalation in the mixture in accordance with a ratio of an output from said sulfide sensor to an output from said humidity sensor; and an alcohol concentration determining unit for determining the concentration of alcohol contained in the exhalation in accordance with a ratio of an output from said alcohol sensor to the output from said humidity sensor.

2. The alcohol measuring apparatus as claimed in claim 1, wherein at least one of said sulfide sensor, humidity sensor and alcohol sensor is covered with a porous membrane to equalize each response time of said sulfide sensor, humidity sensor and alcohol sensor to each detected component of the mixture.

3. The alcohol measuring apparatus as claimed in claim 1, further comprising a valve with one opening connected to said air passage upstream of said sensors and a suction pipe with one end thereof connected to the other opening of said valve, the other end of said suction pipe being open toward a space from which no exhalation is suctioned.

4. The alcohol measuring apparatus as claimed in claim 1, wherein said air passage has an inlet adapted to be positioned where the exhalation to be measured would reach, said humidity sensor being provided downstream of said inlet in said air passage, said alcohol sensor being provided downstream of said humidity sensor inside said air passage.

5. The alcohol measuring apparatus as claimed in claim 4, wherein said humidity sensor is attached at a position opposite to a position where said alcohol sensor is attached so that said alcohol sensor and said humidity sensor protrude in opposite directions.

* * * * *